United States Patent [19]

Goel

[11] 3,951,982

[45] Apr. 20, 1976

[54] TRIALKYLSILYL ESTERS OF 6(SUBSTITUTED AMINO)PHENYL-1,-DIHYDRO-2-OXONICOTINIC ACID, METHODS FOR THEIR PRODUCTION AND CONVERSION TO THE CORRESPONDING ACID CHLORIDES

[75] Inventor: Om P. Goel, Detroit, Mich.

[73] Assignee: Parke, Davis & Company, Jospeh Campau at the River

[22] Filed: Nov. 21, 1974

[21] Appl. No.: 526,017

[52] U.S. Cl................... 260/268 PH; 260/239.1; 260/243 C; 260/247.2 A; 260/247.2 B; 260/293.64; 260/293.69; 260/295.5 R; 424/250
[51] Int. Cl.²....................................... C07D 295/12
[58] Field of Search............. 260/247.2 A, 247.2 B, 260/268 PH, 293.64, 293.69, 295.5 R

[56] References Cited

UNITED STATES PATENTS

| | | | |
|---|---|---|---|
| 3,249,622 | 5/1966 | Herrling et al................... | 260/239.1 |
| 3,478,018 | 11/1969 | Robinson et al................ | 260/239.1 |
| 3,809,699 | 5/1974 | Toshiyasu Ishimaru......... | 260/239.1 |

*Primary Examiner*—R. J. Gallagher
*Assistant Examiner*—Jose Tovar

[57] ABSTRACT

Trialkylsilyl esters of 6-(substituted amino)phenyl-1,2-dihydro-2-oxonicotinic acid and acid addition salts thereof are disclosed. The compounds are useful intermediates in the preparation of pharmacological agents, especially antimicrobials of the penicillin or cephalosporin type. The compounds can be produced by reacting a 6-(substituted amino)phenyl-1,2-dihydro-2-oxonicotinic acid with a silylating agent and are converted to the useful corresponding acid chloride by reaction with thionyl chloride.

7 Claims, No Drawings

TRIALKYLSILYL ESTERS OF 6(SUBSTITUTED AMINO)PHENYL-1,-DIHYDRO-2-OXONICOTINIC ACID, METHODS FOR THEIR PRODUCTION AND CONVERSION TO THE CORRESPONDING ACID CHLORIDES

SUMMARY AND DETAILED DESCRIPTION

The present invention relates to novel chemical compounds that are useful as intermediates in the preparation of pharmacological agents, methods for their production, and methods for their conversion into the corresponding acid chloride which also is a useful intermediate in the preparation of pharmacological agents. More particularly, the invention relates to new trialkylsilyl esters of 6-(substituted amino)-phenyl-1,2-dihydro-2-oxonicotinic acids having the formula

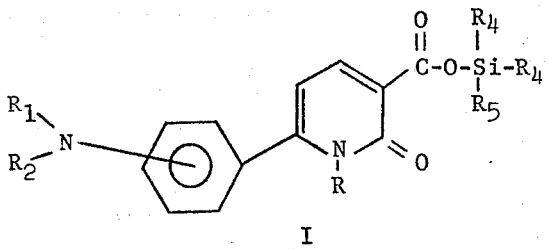

wherein R is hydrogen or methyl; $R_1$ and $R_2$ are branched or straight chain lower alkyl groups of from one to six carbon atoms, or $R_1R_2N$ taken together is 4-$R_3$-1-piperazino, 4-methyl-1-homopiperazino, 1-pyrrolidino, morpholino, 1-piperidino, 4-(1-pyrrolidino)-piperidino or 4-(1-piperidino)piperidino, wherein $R_3$ is a branched or straight chain lower alkyl group of from one to six carbon atoms, cyclohexyl, benzyl, phenyl, halophenyl wherein halo represents chloro, fluoro, bromo, or iodo, and $R_4$ and $R_5$ are each methyl or ethyl and acid addition salts thereof.

The preferred compounds of this invention are those wherein R is hydrogen; $R_1R_2N$ taken together is 4-$R_3$-1-piperazino and $R_3$ is a straight or branched lower alkyl group of from one to six carbon atoms or benzyl. The most preferred embodiments of this process are those wherein the $R_1R_2N$ group is in the para position.

Typical acid addition salts are the hydrochloride, hydrobromide, sulfate, phosphate, acetate or benzoate salts with the preferred salt being the hydrochloride salt.

The compounds of the invention can exist in anhydrous form, as well as in solvated forms. In general, the solvated forms are equivalent to the anhydrous or unsolvated forms for the purposes of the invention.

In addition, this invention relates to a process for the conversion of the compounds of this invention into the corresponding acid chlorides having the formula

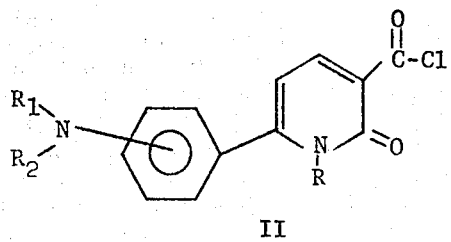

and acid addition salts thereof wherein R, $R_1$ and $R_2$ are as previously defined; which comprises reacting a compound of the invention having the formula

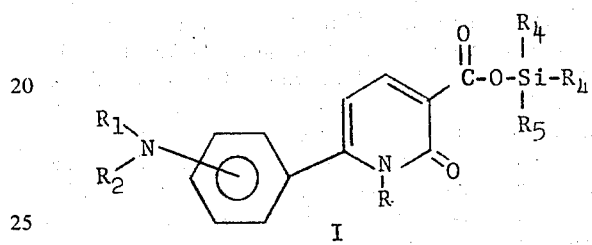

or an acid addition salt thereof, wherein R, $R_1$, $R_2$, $R_4$, and $R_5$ are as previously defined; with thionyl chloride.

This reaction is carried out in an anhydrous inert solvent. Typical solvents would be hydrocarbons such as benzene, toluene, xylene and cyclohexane; chlorinated hydrocarbons such as dichloromethane, 1,2-dichloroethane, chloroform, carbon tetrachloride and chlorobenzene; ethers such as dioxane, tetrahydrofuran, 1,2-dimethoxyethane, dibutyl ether and diethylene glycol dimethyl ether. The reaction temperatures and times are not critical; however, temperatures of from −20° to 40° C. are generally employed for periods of from 1 to 24 hours, preferably temperatures of from 0° to 20° C. While equimolar quantities of reactants may be employed, a slight excess of thionyl chloride, such as 5 percent is preferred.

When a compound of formula I (free base) is employed, the compound isolated is the corresponding acid chloride. The acid chloride may be converted to the corresponding acid addition salt of the acid chloride by the addition of an acid, such as hydrochloric acid, sulfuric acid, phosphoric acid, acetic acid, benzoic acid, etc. Upon employing an acid addition salt of a compound of formula I, the corresponding acid addition salt of the acid chloride is obtained directly.

The compounds of formula I are prepared by reacting a compound having the formula

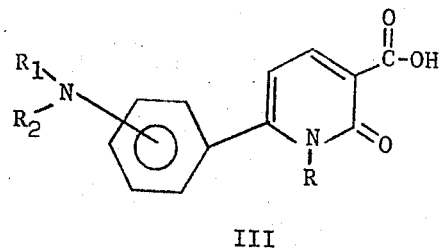

or an acid addition salt thereof wherein R, $R_1$ and $R_2$ are as previously defined with a silylating agent, preferebly hexaalkyldisilazanes, wherein alkyl is methyl or ethyl, such as hexamethyldisilazane, hexaethyldisilazane, 1,3-diethyl-1,1,3,3-tetramethyldisilazane and 1,1,3,3-tetraethyl-1,3-dimethyldisilazane; trialkylchlorosilanes wherein alkyl is methyl or ethyl, such as chlorotrimethylsilane and chlorotriethylsilane.

This reaction is generally carried out in a nonhydroxylic, anhydrous, inert solvent such as a hydrocarbon (benzene, toluene, xylene, cyclohexane, etc.); a chlorinated hydrocarbon (dichloromethane, 1,2-dichloroethane, chloroform, carbon tetrachloride, chlorobenzene, etc.); or an ether (dioxane, tetrahydrofuran, 1,2-dimethoxyethane, dibutyl ether, diethyleneglycol dimethyl ether. When using a hexaalkyldisilazane as the silylating agent, an excess may be used as the solvent; however, this is not preferred since disilylation has been found to complicate the reaction. The reaction temperatures and times are not critical and the selection of these variables would depend largely on the silylating agent used; however, temperatures of from 50° to 150° C. for a period of from 1 to 24 hours are generally employed when using hexaalkyldisilazane. When usng a trialkylchlorosilane as the silylating agent, generally a temperature of from 0° to 50° C. for a period of from 30 minutes to 24 hours may be used. As a rule the lower the temperature, the longer the time allowed for reaction. At a minimum, one equivalent of silylating agent is used to that of a compound of formula III, preferably a moderate excess of silylating agent is used, such as 10 percent.

When a compound of formula III (free base) is silylated using a hexaalkyldisilazane, the product obtained is the compound of formula I in the form of its free base. This compound may be converted to the corresponding compound in the form of its acid addition salt by reaction with an acid, such as hydrochloric acid, sulfuric acid, phosphoric acid, acetic acid, benzoic acid, etc. However, when a compound of formula III (free base) is silylated using a trialkylchlorosilane, the hydrochloride salt of a compound of formula I is obtained directly.

The 6-[(substituted amino)phenyl]-1,2-dihydro-2-oxonicotinic acid compounds (III) which are required as starting materials in the foregoing process can be prepared according to any of a variety of methods as illustrated in greater detail hereinafter.

A compound of the formula

IV is prepared by alkylating a compound of the formula

V with an alkylating agent, such as an alkyl iodide or dialkyl sulfate; or reacting a compound of the formula

VI wherein the fluorine is in the ortho or para position, with an amine of the formula

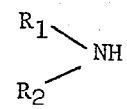

In order to obtain meta disubstituted aminoacetophenones, the procedure shown in Compt. rend. 235, 546 (1952), which is incorporated by reference, may be employed.

The compound of the formula

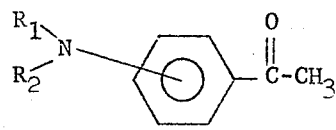

IV is reacted with a lower alkyl formate, such as ethyl formate, in the presence of a strong base, such as sodium methoxide or sodium hydride, to give the sodium salt of the following dicarbonyl compound

VII

This compound in turn is reacted with 2-cyanoacetamide in the presence of piperidine acetate or a reagent which adjusts the pH to about 9 to give the following nitrile

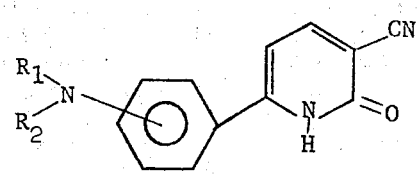

VIII

The above nitrile may also be prepared by reacting a compound of the formula

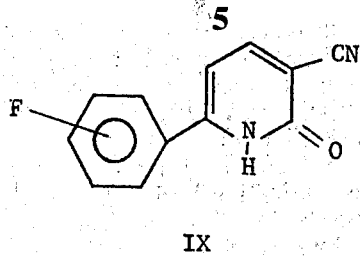

IX wherein the fluorine is in the ortho or para position, with a compound of the formula

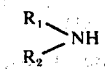

If desired, the resulting nitrile may be methylated utilizing methyl iodide/possium hydroxide to give a compound of the formula

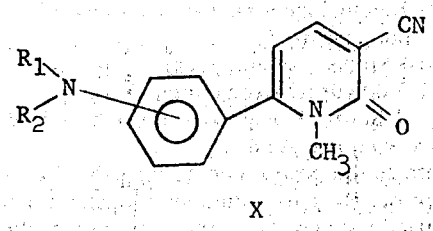

X

Compounds of the formula

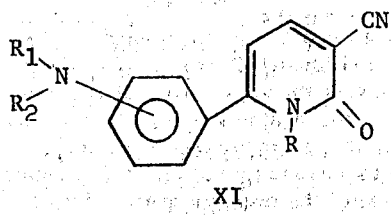

XI wherein R, $R_1$ and $R_2$ are as previously defined, which are prepared by the above procedures, are converted to the desired 6-[(substituted amino)phenyl]-1,2-dihydro-2-oxonicotinic acid by conversion of the cyano group to a carboxyl group utilizing an aqueous solution of a strong base. After neutralization of the free base, one obtains the free acid of the formula III.

The acid chlorides (II) and acid addition salts thereof prepared according to the above described process, when reacted with ampicillin (XII), cephalexin (XIII), or cephaloglycin (XIV) or the acid salt or silylated derivative thereof give rise to a compound of the following structure

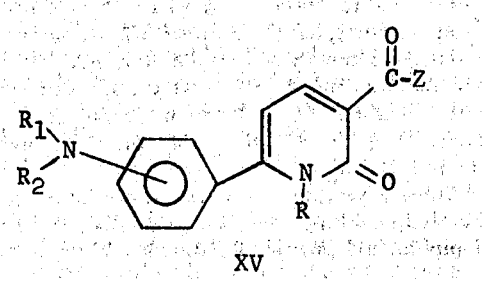

XV wherein R, $R_1$ and $R_2$ are as previously defined and Z is

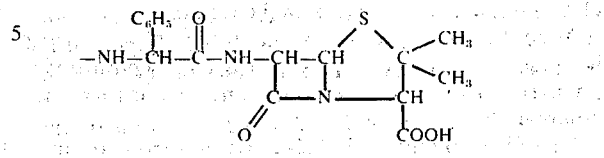

XII

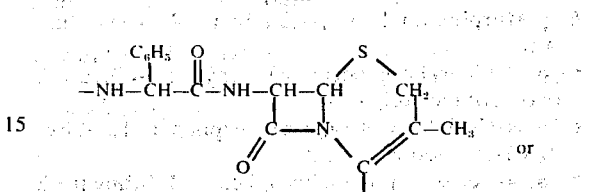

XIII or

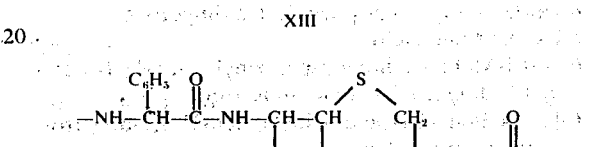

XIV

The above described products, and salts thereof, which are the subject matter of co-pending U.S. patent application Ser. No. 434,763, filed Jan. 21, 1974, now abandoned, which is incorporated by reference, are potent antimicrobial agents. More specifically, these compounds exhibit marked antimicrobial activity against *Klebsiella pneumoniae*, *Serratia marcescens*, *Enterobacter aerogenes* and *Pseudomonas aeruginosa*.

A second method for preparing compounds of the formula XV from acid chlorides of the formula II utilizes an activated form of D(−)-α-phenylglycine, such as D-N-(trimethylsilyl)-2-phenylglycine, trimethylsilyl ester (U.S. patent application Ser. No. 434,763, filed Jan. 21, 1974).

The compound of formula II is coupled to the activated form of D(−)-α-phenylglycine in the presence of triethylamine to give D(+)-N-[6-[p-(4-methyl-1-piperazinyl)-phenyl]-1,2-dihydro-2-oxonicotinyl]-2-phenylglycine (XVI). The phenylglycine derivative XVI is converted to its mixed anhydride by reaction with a compound such as isobutylchloroformate in the presence of a base and the resultant mixed anhydride is reacted with an activated derivative of 6-aminopenicillanic acid, (6-aminopenicillanic acid trimethylsilyl ester), 7-aminocephalosporanic acid or 7-amino-3-methyl-ceph-3-em-4-carboxylic acid to give a product of the formula XV.

The invention is illustrated by the following examples.

EXAMPLE 1

A stirred suspension of 9.39 g. of 1,2-dihydro-6-[p-(4-methyl-1-piperazinyl)phenyl]-2-oxonicotinic acid in 150 ml. of dry dichloromethane is treated under nitrogen with 4.2 ml. of chlorotrimethylsilane. The suspension is stirred at room temperature for 45 minutes, treated with 2.34 ml. of thionyl chloride, and stirred an additional 18 hours. The resulting precipitate of 1,2- dihydro-6-[p-(4-methyl-1-piperazinyl)phenyl]-2-oxonicotinyl chloride, hydrochloride is collected by filtration under nitrogen, washed thoroughly with dichloromethane and dried at reduced pressure.

According to the above procedure, upon substituting in place of 1,2-dihydro-6-[p-(4-methyl-1-piperazinyl)-phenyl]-2-oxonicotinic acid any one of the following compounds 6-(p-Piperidinophenyl)-1,2-dihydro-2-oxonicotinic Acid.

6-(p-Morpholinophenyl)-1,2-dihydro-2-oxonicotinic Acid.

6-[p-(4-Piperidinopiperidino)phenyl]-1,2-dihydro-2-oxonicotinic Acid.

6-[p-(4-Cyclohexyl-1-piperazinyl)phenyl]-1,2-dihydro-2-oxonicotinic Acid.

6-[p-(4-Benzyl-1-piperazinyl)phenyl]-1,2-dihydro-2-oxonicotinic Acid.

6-(m-Dimethylaminophenyl)-1,2-dihydro-2-oxonicotinic Acid.

6-[o-(4-Methyl-1-homopiperazinyl)phenyl]-1-methyl-1,2-dihydro-2-oxonicotinic Acid.

6-[m-(4-Benzyl-1-piperazinyl)phenyl]-1,2-dihydro-2-oxonicotinic Acid.

one obtains the corresponding acid chloride hydrochloride.

The same final product is obtained by substituting an equivalent quantity of chlorotriethylsilane for the chlorotrimethylsilane, above.

EXAMPLE 2

A slurry of 9.4 g. of 1,2-dihydro-6-[p-(4-methyl-1-piperazinyl)phenyl]-2-oxonicotinic acid and 2.7 g. (3.45 ml.) of hexamethyldisilazane in 210 ml. of dry 1,2-dichloroethane is refluxed for 16 hours. The reaction mixture is evaporated to dryness. The residual solid is collected by filtration with the aid of n-heptane, washed with n-heptane and dried at reduced pressure, m.p. > 100° (dec.).

According to the above procedure, upon substituting in place of 1,2-dihydro-6-[p-(4-methyl-1-piperazinyl)-phenyl]-2-oxonicotinic acid any one of the following compounds 6-(p-Piperidinophenyl)-1,2-dihydro-2-oxonicotinic Acid.

6-(p-Morpholinophenyl)-1,2-dihydro-2-oxonicotinic Acid.

6-[p-(4-Piperidinopiperidino)phenyl]-1,2-dihydro-2-oxonicotinic Acid.

6-[p-(4-Cyclohexyl-1-piperazinyl)phenyl]-1,2-dihydro-2-oxonicotinic Acid.

6-[p-(4-Benzyl-1-piperazinyl)phenyl]-1,2-dihydro-2-oxonicotinic Acid.

6-(m-Dimethylaminophenyl)-1,2-dihydro-2-oxonicotinic Acid.

6-[o-(4-Methyl-1-homopiperazinyl)phenyl]-1-methyl-1,2-dihydro-2-oxonicotinic Acid.

6-[m-(4-Benzyl-1-piperazinyl)phenyl]-1,2-dihydro-2-oxonicotinic Acid.

one obtains the corresponding trimethylsilyl ester. By substituting 4.1 g. of hexaethyldisilazane for the hexamethyldisilazane, above, one obtains the corresponding triethylsilyl ester.

EXAMPLE 3

A slurry of 6.26 g. of 1,2-dihydro-6-[p-(4-methyl-1-piperazinyl)phenyl]-2-oxonicotinic acid in 100 ml. of dichloromethane is treated under nitrogen with 4.8 g. of chlorotrimethylsilane. The mixture is stirred at room temperature for 3 hours and the resulting precipitate of 1,2-dihydro-6-[p-(4-methyl-1-piperazinyl)phenyl]-2-oxonicotinic acid, trimethylsilyl ester, monohydrochloride is collected by filtration under nitrogen, washed thoroughly with dichloromethane and dried at reduced pressure under nitrogen at 45° C. for 18 hours.

According to the above procedure, upon substituting in place of 1,2-dihydro-6-[p-(4-methyl-1-piperazinyl)-phenyl]-2-oxonicotinic acid any one of the following compounds 6-(p-Piperidinophenyl)-1,2-dihydro-2-oxonicotinic Acid.

6-(p-Morpholinophenyl)-1,2-dihydro-2-oxonicotinic Acid.

6-[p-(4-Piperidinopiperidino)phenyl]-1,2-dihydro-2-oxonicotinic Acid.

6-[p-(4-Cyclohexyl-1-piperazinyl)phenyl]-1,2-dihydro-2-oxonicotinic Acid.

6-[p-(4-Benzyl-1-piperazinyl)phenyl]-1,2-dihydro-2-oxonicotinic Acid.

6-(m-Dimethylaminophenyl)-1,2-dihydro-2-oxonicotinic Acid.

6-[o-(4-Methyl-1-homopiperazinyl)phenyl]-1-methyl-1,2-dihydro-2-oxonicotinic Acid.

6-[m-(4-Benzyl-1-piperazinyl)phenyl]-1,2-dihydro-2-oxonicotinic Acid.

one obtains the corresponding trimethylsilyl ester hydrochloride. By substituting an equivalent amount of chlorotriethylsilane for the chlorotrimethylsilane, above, one obtains the corresponding triethyl silyl ester hydrochloride.

EXAMPLE 4

A suspension of 9.4 g. of 1,2-dihydro-6-[p-(4-methyl-1-piperazinyl)phenyl]-2-oxonicotinic acid in 210 ml. of dry dichloromethane is stirred at room temperature under a nitrogen atmosphere. Chlorotrimethylsilane, 4.2 ml., is added and mixture is stirred for 40 minutes, followed by the addition of dry triethylamine, 4.2 ml., and stirring of the resultant mixture for 45 minutes.

After cooling the mixture to 3° C., 2.35 ml. of thionyl chloride is added causing the precipitation of an orange solid, 1,2-dihydro-6-[p-(4-methyl-1-piperazinyl)-phenyl]-2-oxonicotinylchloride, and followed by additional stirring at 3° C. for 2.5 hours.

A mixture of 5.0 g. D(−)α-phenylglycine, 7.5 g. (8.76 ml.) chlorotrimethylsilane and 7.14 g. (9.8 ml.) of triethylamine in 150 ml. of dry dichloromethane is stirred under nitrogen for 2 hours. The solution containing D-N-(trimethylsilyl)-2-phenylglycine, trimethylsilylester is filtered in a dry box.

The above solution is added at 3°–5° C. to 1,2-dihydro-6-[p-(4-methyl-1-piperazinyl)phenyl]-2-oxonicotinyl chloride prepared as described. A solution of 4.2 ml. of triethylamine in 22 ml. of dichloromethane is added over a one hour period at 3°–5° C. The reaction solution is allowed to stir at room temperature for 3 hours. The reaction product D(+)-N-[6-[p-(4-methyl-1-piperazinyl)phenyl]1,2dihydro-2-oxonicotinyl]-2-phenylglycine may be isolated, if desired, by dilution of the reaction mixture with water, adjusting pH to 6.0 and filtration. Melting point (capillary) 210°–212° (dec.); $[\alpha]_D^{25}$ + 102° (1% solution in 3:1 dimethylformamide:pyridine).

Alternatively, the above reaction mixture containing, before quenching with water, D(+)-N-[6-[p-(4-methyl-1-piperazinyl)phenyl]-1,2-dihydro-2-oxonicotinyl]-N-

(trimethylsilyl)-2-phenylglycine, trimethylsilylester is cooled to 0° C. and 9 ml. of N-methylformamide added, followed by a dropwise addition of a mixture containing 20 ml. of dimethylformamide, 1.8 ml. of water and 10.5 ml. of N-methylmorpholine. The reaction mixture is stirred at 0° C. for 30 minutes and then cooled to −40° C. Isobutylchloroformate (4.75 ml.) is added and the mixture stirred at −40° C. for 4 minutes. The mixture containing the mixed anhydride of D-(+)-N-[6-p-(4-methyl-1-piperazinyl)phenyl]-1,2-dihydro-2-oxonicotinyl]-2-phenylglycine and carbonic acid monoisobutyl ester, is treated with a solution of 0.03 mole 6aminopenicillanic acid trimethylsilylester [Glombitza, Ann. 673, 166 (1964)] in 25 ml. of dichloromethane. The resulting mixture is stirred at −40° C. for 30 minutes followed by one hour without external cooling, then diluted with 750 ml. of ice water. The pH is adjusted, if necessary, to 5.8 using triethylamine and the mixture stirred at 5° C. for 20 hours. The precipitate of N-[6-[p-(4-methyl-1-piperazinyl)phenyl]-1,2-dihydro-2-oxonicotinyl]-ampicillin is collected by filtration, washed thoroughly with water and dried. Yield: 17.2 g. (89%). % $H_2O$ 7.9. $[\alpha]_D^{25}$ + 147° (1% solution in 75% DMF − 25% pyridine).

The substituted ampicillin (16.2 g.) prepared as described is added to a solution of 9.55 ml. tri-n-propylamine in 34.5 ml. of acetonitrile. After stirring for three hours, the tri-n-propylamine salt of the substituted ampicillin is filtered off, washed with acetonitrile and dried yielding a yellow crystalline solid, 15.9 g., $[\alpha]_D^{25}$ + 159° (1.03% solution in 75% dimethylformamide− 25% pyridine).

Ten grams of the above tri-n-propylamine salt of the substituted ampicillin is dissolved in 36 ml. of cold (4° C.) 1:1 (v/v) acetonitrile-water. The solution is filtered, the pH adjusted to 5.8 with cold dilute (8.5%) aqueous acetic acid and further diluted with 70 ml. of cold (4° C.) water. The bright yellow product of N-[6-p-(4-methyl-1-piperazinyl)phenyl]-1,2-dihydro-2-oxonicotinyl]ampicillin is collected by filtration, washed with cold water and dried. Wt. 8 g. $[\alpha]_D^{25}$ + 198° (1% solution in 75% dimethyl formamide− 25% pyridine).

EXAMPLE 5

Triethylamine, in the amount of 627 g., is added to a stirred suspension of 2500 g. of ampicillin trihydrate in 28.5 liters of dry acetonitrile which is cooled to 7°–8°. The mixture is stirred for 1.3 hours at 5° and the resulting precipitate of the triethylamine salt of ampicillin is collected by filtration, washed in turn with cold acetonitrile, with ether and with petroleum ether, then dried at reduced pressure.

Chlorotrimethylsilane, in an amount of 103 g., is added to a stirred suspension of 210 g. of the triethylamine salt of ampicillin in 1900 ml. of dichloromethane followed by the addition of 189 ml. of triethylamine. The mixture is stirred at 15° for 30 minutes, then 209 g. of 6-[p-(4-methyl-1-piperazinyl)phenyl]-1,2-dihydro-2-oxonicotinyl chloride hydrochloride is added. The mixture is stirred at room temperature for 16 hours, then diluted with 4 liters of ice water and acidified to a pH of 5.8 with hydrochloric acid. The precipitate of N-[6-(4-methyl-1-piperazinyl)phenyl]-1,2-dihydro-2-oxonicotinyl]ampicillin is collected by filtration and dried. This substituted ampicillin is dissolved in acetonitrile and the solution is treated with one equivalent of triethylamine. The resulting precipitate of the triethylamine salt is collected by filtration and dried. This triethylamine salt is dissolved in 1:1 tetrahydrofuran-acetonitrile and the solution is treated with one equivalent of a 50% solution of sodium 2-ethylhexanoate in 1-butanol. The resulting precipitate of the sodium salt is collected by filtration, washed with ether and dried; $[\alpha]_d^{25}$ + 188° (1.02% in 3:1 dimethylformamide-pyridine).

A 250 ml. solution of 0.2N aqueous sodium hydroxide is added carefully to a suspension of 64.5 g. of the substituted ampicillin in 250 ml. of acetone and the mixture stirred at room temperature for 30 minutes. The resulting solution is filtered and the filtrate poured with stirring into 6 liters of acetone. N-[6-]p-(4-Methyl-1-piperazinyl)phenyl]1,2-dihydro-2-oxonicotinyl-]ampicillin in the form of its hemisodium salt (a 1:1 mixture or complex of the substituted ampicillin and its sodium salt) is collected by filtration, washed with acetone and with ether, then dried; $[\alpha]_d^{25}$ + 178° (1.02% in 3:1 dimethylformamide-pyridine).

A solution of 644.7 mg. of N-[6-[p-(4-methyl-1-piperazinyl)phenyl]-1,2-dihydro-2-oxonicotinyl]ampicillin in 10 ml. of dimethylacetamide is filtered and the filtrate treated with 0.25 ml. of a 4.8N solution of hydrogen chloride in isopropanol. Addition of ethyl acetate gives a yellow solid which is collected, washed with ethylacetate and dried. The yellow solid which is obtained in a yield of 668 mg. is shown by analysis to be N-[6-[p-(4-methyl-1-piperazinyl)phenyl]-1,2-dihydro-2-oxonicotinyl]ampicillin monohydrochloride $[\alpha]_d^{25}$ + 139° (0.965% in MeOH).

According to the above procedure, upon substituting in place of 1,2-dihydro-6-[p-(4-methyl-1-piperazinyl)-phenyl]-2-oxonicotinic acid any one of the following compounds

- 6-(p-Piperidinophenyl)-1,2-dihydro-2-oxonicotinyl chloride hydrochloride.
- 6-(p-Morpholinophenyl)-1,2-dihydro-2-oxonicotinyl chloride hydrochloride.
- 6-[p-(4-Piperidinopiperidino)phenyl]-1,2-dihydro-2-oxonicotinyl chloride hydrochloride.
- 6-[p-(4-Cyclohexyl-1-piperazinyl)phenyl]-1,2-dihydro-2-oxonicotinyl chloride hydrochloride.
- 6-[p-(4-Benzyl-1-piperazinyl)phenyl]-1,2-dihydro-2-oxonicotinyl chloride hydrochloride.
- 6-(m-Dimethylaminophenyl)-1,2-dihydro-2-oxonicotinyl chloride hydrochloride.
- 6-[o-(4-Methyl-1-homopiperazinyl)phenyl]-1-methyl-1,2-dihydro-2-oxonicotinyl chloride hydrochloride.
- 6-[m-(4-Benzyl-1-piperazinyl)phenyl]-1,2-dihydro-2-oxonicotinyl chloride hydrochloride.

one obtains the corresponding derivative of ampicillin.

STARTING MATERIALS

The various starting materials employed in the foregoing examples and intermediates required for their preparation are obtained by the methods described in the following.

A. (SUBSTITUTED AMINO)ACETOPHENONES a. p-(4-Methyl-1-piperazinyl)acetophenone.

A solution of 1120 g. of N-methylpiperazine and 755 g. of p-fluoroacetophenone in 1920 ml. of dimethyl-sulfoxide is heated at 95° for 16 hours, then evaporated at reduced pressure. The residue is poured into 8 liters of water and the solution is basified with 440 g. of 50% aqueous sodium hydroxide and cooled. The precipitate of p-(4-methyl-1-piperazinyl)acetophenone is collected by filtration, washed with water and dried; m.p. 97°–99°.

b. p-(4-Propyl-1-piperazinyl)acetophenone.

A mixture of 33.2 g. of p-fluoroacetophenone, 48.3 g. of N-propylpiperazine and 99.5 g. of potassium carbonate in 100 ml. of dimethyl sulfoxide is stirred and heated at 95° for 4.5 hours, then cooled and poured into ice water. The precipitate of p-(4-propyl-1-piperazinyl)acetophenone is collected by filtration, washed with water and dried; m.p. 68°–70° after crystallization from hexane.

c. o-(4-Methyl-1-piperazinyl)acetophenone.

A mixture of 55.2 g. of o-fluoroacetophenone and 100 ml. of N-methyl-piperazine is heated at 95°–100° for 19 hours, then cooled and poured into 1600 ml. of water containing 22 ml. of 50% aqueous sodium hydroxide. The mixture is extracted with three 300 ml. portions of ether. The combined ether extract is washed thoroughly with water, then with saturated aqueous sodium chloride, dried and evaporated to give o-(4-methyl-1-piperazinyl)acetophenone as a viscous oil, suitable for use without further purification.

B.
6-SUBSTITUTED-1,2-DIHYDRO-2-OXONICOTINONITRILES a. 6-[p-(4-Methyl-1-piperazinyl)phenyl]-1,2-dihydro-2-oxonicotinonitrile.

To a stirred suspension of 820 g. of sodium methoxide in 7.5 liters of tetrahydrofuran is added dropwise a solution of 918 g. of ethyl formate and 2.7 kg. of p-(4-methyl-1-piperazinyl)acetophenone in 7 liters of tetrahydrofuran while maintaining the temperature below 11°. The mixture is diluted further with 4 liters of tetrahydrofuran and stirred at room temperature for 16 hours. The resulting precipitate of the sodium salt of p-(4-methyl-1-piperazinyl)benzoylacetaldehyde is collected by filtration, washed with tetrahydrofuran and dried. A solution of this sodium salt in 12 liters of water is treated with 1050 g. of 2-cyanoacetamide and a solution consisting of 130 ml. of acetic acid, 300 ml. of water and 230 ml. of piperidine. The solution is stirred and heated, while allowing tetrahydrofuran to distill until the temperature reaches 92°, and is maintained at this temperature for 3 hours, then allowed to stand at room temperature for 16 hours. The mixture is acidified to pH 6 with acetic acid, then neutralized to pH 7.1 with saturated aqueous sodium bicarbonate. The precipitate of 6-[p-(4-methyl-1-piperazinyl)phenyl]-1,2-dihydro-2-oxonicotinonitrile is collected by filtration, washed with water and dried; m.p. >310° (dec.).

In a similar manner, the following nitriles are prepared:

b. 6-[p-(Dimethylamino)phenyl]-1,2-dihydro-2-oxonicotinonitrile.

From a solution of the sodium salt of p-(dimethylamino)benzoylacetaldehyde in 400 ml. of water (prepared from 11.4 g. of sodium methoxide in 100 ml. of tetrahydrofuran, and a solution of 29.3 g. of p-(dimethylamino)acetophenone [J.A.C.S. 73, 864 (1951)] and 13.3 g. of ethyl formate in 130 ml. of tetrahydrofuran), 18.5 g. of 2-cyanoacetamide and a solution consisting of 2.3 ml. of acetic acid, 5.2 ml. of water and 4.0 ml. of piperidine, there is obtained 6-[p-(dimethylamino)phenyl]-1,2-dihydro-2-oxonicotinonitrile; m.p. 280°–292° (dec.) after crystallization from aqueous dimethyl sulfoxide.

c. 6-[m-(Dimethylamino)phenyl]-1,2-dihydro-2-oxonicotinonitrile.

By substituting the same amount of m-(dimethylamino)acetophenone [Compt. rend. 235, 546 (1952)] for the p-(dimethylamino)acetophenone in b) above, the product obtained is 6-[m-(dimethylamino)phenyl]-1,2-dihydro-2-oxonicotinonitrile; m.p. > 260° (dec.).

d. 6-[p-(4-Propyl-1-piperazinyl)phenyl]-1,2-dihydro-2-oxonicotinonitrile.

From a solution of the sodium salt of p-(4-propyl-1-piperazinyl)benzoylacetaldehyde in 150 ml. of water (prepared from 5.7 g. of sodium methoxide in 500 ml. of tetrahydrofuran, and a solution of 24.6 g. of p-(4-propyl-1-piperazinyl)acetophenone and 8.0 ml. of ethyl formate in 100 ml. of tetrahydrofuran), 8.4 g. of 2-cyanoacetamide and a solution consisting of 0.95 ml. of acetic acid, 4.0 ml. of water and 0.9 ml. of piperidine, there is obtained 6-[p-(4-propyl-1-piperazinyl)phenyl]-1,2-dihydro-2-oxonicotinonitrile; m.p. 288°–290° (dec.).

e. 6-(p-Piperidinophenyl)-1,2-dihydro-2-oxonicotinonitrile.

From a solution of the sodium salt of p-(piperidino)benzoylacetaldehyde in 300 ml. of water (prepared from 11.4 g. of sodium methoxide in 100 ml. of tetrahydrofuran, and a solution of 36.5 g. of p-(piperidino)acetophenone and 13.3 g. of ethyl formate in 130 ml. of tetrahydrofuran), 18.9 g. of 2-cyanoacetamide and a solution consisting of 2.3 ml. of acetic acid, 5.3 ml. of ester and 4.1 ml. of piperidine, there is obtained 6-(p-piperidinophenyl)-1,2-dihydro-2-oxonicotinonitrile.

f. 6-(p-Morpholinophenyl)-1,2-dihydro-2-oxonicotinonitrile.

To a stirred mixture of 38.8 g. of a 57% sodium hydride dispersion in mineral oil and 500 ml. of benzene is added dropwise with cooling a solution of 82.1 g. of p-(morpholino)acetophenone (Brit. Pat. 911,342), 45 ml. of ethyl formate and 2 ml. of ethanol in 300 ml. of benzene. An additional 400 ml. of benzene is added and the suspension is stirred at room temperature for 16 hours, then treated with 1.5 liters of cold water. The aqueous phase, containing the sodium salt of p-(morpholino)benzoylacetaldehyde, is separated and treated successively with 28.6 ml. of acetic acid, 10 ml. of piperidine and 34 g. of 2-cyanoacetamide. The mixture is stirred and heated at reflux for 3 hours, cooled and acidified with acetic acid to pH 5.0. The resulting precipitate of 6-(p-morpholinophenyl)-1,2-dihydro-2-oxonicotinonitrile is collected and triturated with ethyl acetate; m.p. 272°–275° afer two crystallizations from ethanol.

g. 6-[p-(4-Piperidinopiperidino)phenyl]-1,2-dihydro-2-oxonicotinonitrile.

A mixture of 10.7 g. of 6-(p-fluorophenyl)-1,2-dihydro-2-oxonicotinonitrile [J. Med. Chem. 14, 342 (1971)] and 16.8 g. of 4-piperidinopiperidine in 140 ml. of dimethyl sulfoxide is stirred and heated at 95°–100° for 50 hours. The mixture is cooled and diluted with 450 ml. of 95% ethanol. The resulting precipitate of 6-[p-(4-piperidinopiperidino)phenyl]-1,2-dihydro-2-oxonicotinonitrile is collected by filtration, washed with 95% ethanol and dried; m.p. 288°–293° (dec.).

In a similar manner, the following nitriles are prepared:

h. 6-[p-(4-Cyclohexyl-1-piperazinyl)phenyl]-1,2-dihydro-2-oxonicotinonitrile.

From 11.7 g. of 6-(p-fluorophenyl)-1,2-dihydro-2-oxonicotinonitrile and 18.4 g. of N-cyclohexylpiperazine in 150 ml. of dimethyl sulfoxide, there is obtained 6-[p-(4-cyclohexyl-1-piperazinyl)phenyl]-1,2-dihydro-2-oxonicotinonitrile; m.p. 306°–312° (dec.).

i. 6-[p-(4-Benzyl-1-piperazinyl)phenyl]-1,2-dihydro-2-oxonicotinonitrile.

From 11.7 g. of 6-(p-fluorophenyl)-1,2-dihydro-2-oxonicotinonitrile and 19.1 g. of N-benzylpiperazine in 150 ml. of dimethyl sulfoxide, there is obtained 6-[p-(4-benzyl-1-piperazinyl)phenyl]-1,2-dihydro-2-oxonicotinonitrile; m.p. 275°–286° (dec.).

j. 6-[p-(4-Ethyl-1-piperazinyl)phenyl]-1,2-dihydro-2-oxonicotinonitrile.

From 21.4 g. of 6-(p-fluorophenyl)-1,2-dihydro-2-oxonicotinonitrile and 22.8 g. of N-ethylpiperazine in 200 ml. of dimethyl sulfoxide, there is obtained 6-[p-(4-ethyl-1-piperazinyl)phenyl]-1,2-dihydro-2-oxonicotinonitrile; m.p. 283°–285° (dec.).

k. 6-[p-[4-(m-Chlorophenyl)-1-piperazinyl]phenyl]-1,2-dihydro-2-oxonicotinonitrile.

From 12.9 g. of 6-(p-fluorophenyl)-1,2-dihydro-2-oxonicotinonitrile and 23.7 g. of N-(m-chlorophenyl)piperazine in 180 ml. of dimethyl sulfoxide; there is obtained 6-[p-[4-(m-chlorophenyl)-1-piperazinyl]phenyl]-1,2-dihydro-2-oxonicotinonitrile.

l. 6-[p-(4-Phenyl-1-piperazinyl)phenyl]-1,2-dihydro-2-oxonicotinonitrile.

From 12.9 g. of 6-(p-fluorophenyl)-1,2-dihydro-2-oxonicotinonitrile and 19.5 g. of N-phenylpiperazine in 180 ml. of dimethyl sulfoxide, there is obtained 6-[p-(4-phenyl-1-piperazinyl)phenyl]-1,2-dihydro-2-oxonicotinonitrile.

m. 6-[p-[4-(1-Pyrrolidinyl)piperidino]phenyl]-1,2-dihydro-2-oxonicotinonitrile.

From 11.7 g. of 6-(p-fluorophenyl)-1,2-dihydro-2-oxonicotinonitrile and 16.7 g. of 4-(1-pyrrolidinyl)piperidine in 150 ml. of dimethyl sulfoxide, there is obtained 6-[p-[4-(1-pyrrolidinyl)piperidino]phenyl]-1,2-dihydro-2-oxonicotinonitrile; m.p. 318°–326° (dec.).

n. 6-[p-(Hexahydro-4-methyl-1H-1,4-diazepin-1-yl)phenyl]-1,2-dihydro-2-oxonicotinonitrile.

From 12.9 g. of 6-(p-fluorophenyl)-1,2-dihydro-2-oxonicotinonitrile and 13.8 g. of N-methylhomopiperazine in 180 ml. of dimethyl sulfoxide, there is obtained 6-[p-(hexahydro-4-methyl-1H-1,4-diazepin-1-yl)phenyl]-1,2-dihydro-2-oxonicotinonitrile.

o. 6-[p-(4-Methyl-1-piperazinyl)phenyl]-1,2-dihydro-1-methyl-2-oxonicotinonitrile.

A mixture of 9.1 g. of 6-[p-(4-methyl-1-piperazinyl)phenyl]-1,2-dihydro-2-oxonicotinonitrile, 2.0 g. of potassium hydroxide, 5.0 ml. of iodomethane and 250 ml. of absolute ethanol is stirred and heated at reflux for 5 hours, then evaporated at reduced pressure. The residue is washed thoroughly with warm water, then dried, to give 6-[p-(4-methyl-1-piperazinyl)phenyl]-1,2-dihydro-1-methyl-2-oxonicotinonitrile as the remaining solid.

p. 6-[o-(4-Methyl-1-piperazinyl)phenyl]-1,2-dihydro-2-oxonicotinonitrile.

To a stirred suspension of 22.9 g. of sodium methoxide in 500 ml. of dry ether is added dropwise at 7°–10° a solution of 40.3 g. of ethyl formate and 79.3 g. of o-(4-methyl-1-piperazinyl)acetophenone in 150 ml. of dry ether. The mixture is stirred at room temperature for 17 hours, then extracted three times with 300 ml. portions of water. The combined aqueous extract, containing the sodium salt of o-(4-methyl-1-piperazinyl)benzoylacetaldehyde, is adjusted to pH 9 with acetic acid, treated with 45.8 g. of 2-cyanoacetamide and stirred and heated at 90°–95° for 6 hours. The mixture is cooled and the precipitate of 6-[o-(4-methyl-1-piperazinyl)phenyl]-1,2-dihydro-2-oxonicotinonitrile is collected by filtration, washed with water and dried; m.p. 202°–203° after crystallization from ethyl acetate.

C.

6-SUBSTITUTED-1,2-DIHYDRO-2-OXONICOTINIC ACIDS a. 6-[p-(4-Methyl-1-piperazinyl)phenyl]-1,2-dihydro-2-oxonicotinic Acid.

A mixture of 457 g. of 6-[p-(4-methyl-1-piperazinyl)phenyl]-1,2-dihydro-2-oxonicotinonitrile and 4570 g. of 20% aqueous potassium hydroxide is heated at 105° in an agitated stainless steel autoclave for 40 hours, then poured into a mixture of 1.4 kg. of ice and 1.4 liters of concentrated hydrochloric acid. The pH of the resulting mixture is adjusted to pH 6.5 with 5% aqueous sodium hydroxide and the precipitate of 6-[p-(4-methyl-1-piperazinyl)phenyl[-1,2-dihydro-2-oxonicotinic acid is collected by filtration, washed with water, then with 95% ethanol, and dried; m.p. 300° (dec.).

In a similar manner the following acids are prepared by hydrolysis of the corresponding nitrile with ten times its weight of 20% aqueous potassium hydroxide, followed by acidification and suitable adjustment of the pH.

b. 6-[p-(Dimethylamino)phenyl]-1,2-dihydro-2-oxonicotinic Acid.

c. 6-[m-(Dimethylamino)phenyl]-1,2-dihydro-2-oxonicotinic Acid [m.p. 275°–280° (dec.) after crystallization from aqueous dimethyl sulfoxide.]

d. 6-[p-(4-Propyl-1-piperazinyl)phenyl]-1,2-dihydro-2-oxonicotinic Acid [m.p. 268°–269° (dec.).]

e. 6-(p-Piperidinophenyl)-1,2-dihydro-2-oxonicotinic Acid.

f. 6-(p-Morpholinophenyl)-1,2-dihydro-2-oxonicotinic Acid [m.p.>300° (dec.).]

g. 6-[p-(4-Piperidinopiperidino)phenyl]-1,2-dihydro-2-oxonicotinic Acid.

h. 6-[p-(4-Cyclohexyl-1-piperazinyl)phenyl]-1,2-dihydro-2-oxonicotinic Acid [m.p. 300°–305° (dec.).]

i. 6-[p-(4-Benzyl-1-piperazinyl)phenyl]-1,2-dihydro-2-oxonicotinic Acid [m.p. 276°–280° (dec.).

j. 6-[p-(4-Ethyl-1-piperazinyl)phenyl]-1,2-dihydro-2-oxonicotinic Acid [m.p. 295°–296°.]

k. 6-[p-[4-(m-Chlorophenyl)-1-piperazinyl]phenyl]-1,2-dihydro-2-oxonicotinic Acid.

l. 6-[p-(4-Phenyl-1-piperazinyl)phenyl]-1,2-dihydro-2-oxonicotinic Acid.

m. 6-[p-[4-(1-Pyrrolidinyl)piperidino]phenyl]-1,2-dihydro-2-oxonicotinic Acid.

n. 6-[p-(Hexahydro-4-methyl-1H-1,4-diazepin-1-yl)phenyl]-1,2-dihydro-2-oxonicotinic Acid.

o. 6-[p-(4-Methyl-1-piperazinyl)phenyl]-1,2-dihydro-1-methyl-2-oxonicotinic Acid.

p. 6-[o-(4-Methyl-1-piperazinyl)phenyl]-1,2-dihydro-2-oxonicotinic Acid.

A mixture of 14.7 g. of 6-[o-(4-Methyl-1-piperazinyl)phenyl]-1,2-dihydro-2-oxonicotinonitrile and 246 ml. of 17% aqueous sodium hydroxide is stirred and heated at reflux 43 hours, then filtered hot.

The filtrate is poured into a solution of 63 ml. of concentrated hydrochloric acid in 350 ml. of ice water. The resulting precipitate of 6-[o-(4-methyl-1-piperazinyl)phenyl]-1,2-dihydro-2-oxonicotinic acid is collected by filtration, washed with water and dried; m.p. 214.5°–215.5° (dec.) after

I claim:

1. A member of the class consisting of compounds of the formula

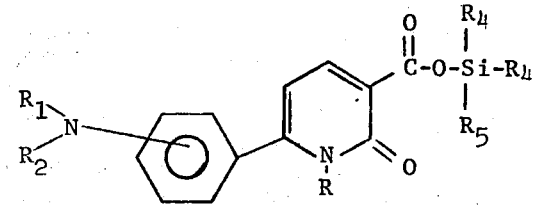

or acid addition salts thereof, wherein R is hydrogen or methyl; $R_1$ and $R_2$ are branched or straight chain lower alkyl groups of from one to six carbon atoms, or $R_1R_2N$ taken together form 4-$R_3$-1-piperazino, 4-methyl-1-homopiperazino, 1-pyrrolidino, morpholino, 1-piperidino, 4-(1-pyrrolidino)-piperidino or 4-(1-piperidino)piperidino, wherein $R_3$ is a lower alkyl group of from one to six carbon atoms, cyclohexyl, benzyl, phenyl, halophenyl wherein halo represents chloro, fluoro, bromo, or iodo, and $R_4$ and $R_5$ are each methyl or ethyl.

2. A compound according to claim 1 wherein $R_1R_2N$ taken together is a p-(4-methyl-1-piperazinyl) group.

3. A compound according to claim 2 wherein $R_4$ and $R_5$ are methyl.

4. A compound according to claim 2 wherein $R_4$ and $R_5$ are ethyl.

5. A process for the production of 6-(disubstituted amino)phenyl-1,2-dihydro-2-oxonicotinyl chloride having the formula

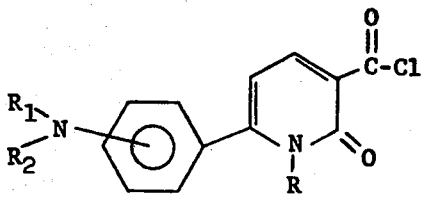

or a salt thereof which comprises reacting a compound of the formula,

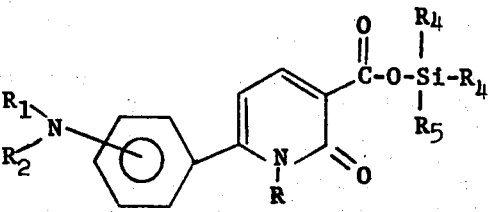

or acid addition salts thereof, with thionyl chloride wherein R, $R_1$, $R_2$, $R_4$, and $R_5$ are as defined in claim 1.

6. The process of claim 5 wherein $R_1R_2N$ taken together is a p-(4-methyl-1-piperazinyl) group.

7. The process of claim 5 wherein the silyl ester employed is in the form of the free base.

* * * * *